US011458302B2

(12) United States Patent
Chavez

(10) Patent No.: US 11,458,302 B2
(45) Date of Patent: Oct. 4, 2022

(54) HINGED LEAD FIXATION DEVICES FOR SECURING A LEAD TO A CRANIUM

(71) Applicant: NeuroPace, Inc., Mountain View, CA (US)

(72) Inventor: Alfonso Chavez, San Jose, CA (US)

(73) Assignee: NeuroPace, Inc., Mountain View, CA (US)

( * ) Notice: Subject to any disclaimer, the term of this patent is extended or adjusted under 35 U.S.C. 154(b) by 2 days.

(21) Appl. No.: 17/096,773

(22) Filed: Nov. 12, 2020

(65) Prior Publication Data

US 2021/0170166 A1   Jun. 10, 2021

Related U.S. Application Data

(60) Provisional application No. 62/943,698, filed on Dec. 4, 2019.

(51) Int. Cl.
*A61N 1/05* (2006.01)
*A61N 1/375* (2006.01)

(52) U.S. Cl.
CPC ......... *A61N 1/0539* (2013.01); *A61N 1/0534* (2013.01); *A61N 1/37518* (2017.08)

(58) Field of Classification Search
CPC . A61N 1/0539; A61N 1/37518; A61N 1/0534
See application file for complete search history.

(56) References Cited

U.S. PATENT DOCUMENTS

| | | | |
|---|---|---|---|
| 4,328,813 A | 5/1982 | Ray | |
| 5,464,446 A | 11/1995 | Dreesen et al. | |
| 5,843,150 A | 12/1998 | Dressen et al. | |
| 5,865,842 A | 2/1999 | Knuth et al. | |
| 5,865,843 A | 2/1999 | Baudino | |
| 5,927,277 A | 7/1999 | Baudino et al. | |

(Continued)

FOREIGN PATENT DOCUMENTS

| | | |
|---|---|---|
| WO | 2001176498 A2 | 10/2001 |
| WO | 2004103468 A1 | 12/2014 |

OTHER PUBLICATIONS

Biomet Microfixation. Neuroimplant System. Product Brochure (2013).

(Continued)

*Primary Examiner* — Eric D. Bertram
(74) *Attorney, Agent, or Firm* — Loza & Loza, LLP; David S. Sarisky

(57) ABSTRACT

A lead fixation device for securing a portion of a lead relative to a surface of a skull includes a skull attachment member having an upper surface and a lower surface, a locking member having an upper surface and a lower surface and associated with the skull attachment member, and a passageway associated with the locking member and configured to receive the portion of the lead. The skull attachment member and the locking member are configured to rotate relative to each other to transition the lead fixation device between a closed state wherein the lower surface of the skull attachment member and the lower surface of the locking member are generally aligned in a common plane, and an opened state wherein the lower surface of the skull attachment member and the lower surface of the locking member are not aligned in a common plane.

15 Claims, 10 Drawing Sheets

(56) References Cited

U.S. PATENT DOCUMENTS

| | | | |
|---|---|---|---|
| 6,044,304 A | 3/2000 | Baudino | |
| 6,134,477 A | 10/2000 | Knuteson et al. | |
| 6,210,417 B1 | 4/2001 | Baudino et al. | |
| 6,319,241 B1 | 11/2001 | King et al. | |
| 6,321,104 B1 | 11/2001 | Gielen et al. | |
| 6,356,792 B1 * | 3/2002 | Errico | A61N 1/0534 606/129 |
| 6,795,737 B2 | 9/2004 | Gielen et al. | |
| 6,810,285 B2 | 10/2004 | Pless et al. | |
| 6,902,569 B2 | 6/2005 | Parmer et al. | |
| 7,204,840 B2 | 4/2007 | Skakoon et al. | |
| 7,235,084 B2 | 6/2007 | Skakoon et al. | |
| 7,580,756 B2 | 8/2009 | Schulte et al. | |
| 7,604,644 B2 | 10/2009 | Schulte et al. | |
| 7,636,596 B2 | 12/2009 | Solar | |
| 7,637,915 B2 | 12/2009 | Parmer et al. | |
| 7,660,621 B2 | 2/2010 | Skakoon et al. | |
| 7,704,260 B2 | 4/2010 | Skakoon et al. | |
| 7,744,606 B2 | 6/2010 | Miller et al. | |
| 7,766,394 B2 | 8/2010 | Sage et al. | |
| 7,766,922 B1 | 8/2010 | Daglow et al. | |
| 7,815,651 B2 | 10/2010 | Skakoon et al. | |
| 7,828,809 B2 | 11/2010 | Skakoon et al. | |
| 7,833,231 B2 | 11/2010 | Skakoon et al. | |
| 7,857,820 B2 | 12/2010 | Skakoon et al. | |
| 7,949,410 B2 | 5/2011 | Rodriguez | |
| 7,976,530 B2 | 7/2011 | Johnson et al. | |
| 7,988,674 B2 | 8/2011 | Adams et al. | |
| 8,116,850 B2 | 2/2012 | Solar | |
| 8,152,792 B1 | 4/2012 | Kornel | |
| 8,192,445 B2 | 6/2012 | Parmer et al. | |
| 8,845,656 B2 | 9/2014 | Skakoon et al. | |
| 8,911,452 B2 | 12/2014 | Skakoon et al. | |
| 9,545,509 B2 | 1/2017 | Greene | |
| 9,572,973 B2 | 2/2017 | Chavez et al. | |
| 2005/0015128 A1 | 1/2005 | Rezai et al. | |
| 2005/0182420 A1 * | 8/2005 | Schulte | A61N 1/0539 606/130 |
| 2005/0182421 A1 | 8/2005 | Schulte et al. | |
| 2005/0182422 A1 | 8/2005 | Schulte et al. | |
| 2005/0182424 A1 | 8/2005 | Schulte et al. | |
| 2005/0182425 A1 | 8/2005 | Schulte et al. | |
| 2009/0112327 A1 | 4/2009 | Lane et al. | |
| 2009/0306750 A1 | 12/2009 | Boling et al. | |
| 2009/0326610 A1 | 12/2009 | Pless et al. | |
| 2010/0179563 A1 | 7/2010 | Skakoon et al. | |
| 2010/0268308 A1 * | 10/2010 | Rossby | A61B 90/10 607/116 |
| 2010/0312193 A1 | 12/2010 | Stratton | |
| 2011/0270187 A1 | 11/2011 | Nelson | |
| 2013/0066410 A1 | 3/2013 | Funderburk | |
| 2014/0257325 A1 * | 9/2014 | Chavez | A61F 2/2875 606/129 |

OTHER PUBLICATIONS

Aesculap Inc. Cranial Fixation Systems. Product Brochure (2014).
Miller et al. "Stereotactic bony trajectory preservation for responsive neurostimulator lead placement following depth EEG recording." Cureus 8(3):3549. DOI 10.7759/cureus.549 (Mar. 30, 2016).
Synthes CMF. "MatrixNEURO. The next generation cranial plating system." Product Brochure (2006).

* cited by examiner

HINGED LEAD FIXATION DEVICES FOR SECURING A LEAD TO A CRANIUM

CROSS-REFERENCE TO RELATED APPLICATION(S)

This application claims the benefit of and priority to U.S. Provisional Patent Application Ser. No. 62/943,698, filed Dec. 4, 2019, for "Hinged Lead Fixation Devices for Securing a Lead to a Cranium," the entire disclosure of which is incorporated herein by reference.

TECHNICAL FIELD

The present disclosure relates generally to apparatuses used when implanting a medical device in a patient, and more particularly, to lead fixation devices for securing a lead to a cranium.

BACKGROUND

Some diagnostic or interventional medical procedures require implanting one or more leads through a hole in a patient's cranium. For example, in the responsive neurostimulation system manufactured under the tradename RNS SYSTEM by NeuroPace, Inc., leads are provided with electrodes configured to sense information from the brain or to deliver a form of stimulation to the brain intended to modulate neural activity, such as electrical stimulation. The sensing and/or stimulation may occur at a distal end of the lead, for example, through electrodes exposed to brain tissue at a distal end, wherein the signals are communicated through conductors disposed in a lead body extending to a lead proximal end. Connections available at the lead proximal end allow the lead to be connected to another medical device that processes the sensed signals and/or generates the form of stimulation.

There are multiple types of brain leads currently available. In applications where the leads are being used to sense or stimulate brain tissue at or near the focus of undesirable epileptiform activity, there is a depth lead (also sometimes referred to as a "deep brain lead" or as a "stereotactic depth lead", because this lead type is often implanted using stereotaxy, a three-dimensional localization and placement procedure) and a cortical strip lead (also known simply as a "cortical lead" or as a "subdural lead", because this lead type is usually implanted underneath the dura mater).

A depth lead is implanted so that the distal end is located in the brain tissue, in or adjacent a structure that is deemed to be associated with the generation of the undesirable activity. A cortical strip lead is implanted so that the distal end lays on a surface of the brain at or adjacent brain tissue that is believed to comprise an epileptic focus. The intended location of the distal end of the brain lead in or on the brain is referred to hereinafter as the "target." Once a lead is placed so that the distal end is at the target location, it is desirable that the lead be secured in place so that the distal end does not migrate from the target location.

SUMMARY

The present disclosure relates to a lead fixation device for securing a portion of a lead relative to a surface of a skull. The device includes a skull attachment member having an upper surface and a lower surface, a locking member having an upper surface and a lower surface and associated with the skull attachment member, and a passageway associated with the locking member and configured to receive the portion of the lead. The skull attachment member and the locking member are coupled together to rotate relative to each other to transition the lead fixation device between a closed state wherein the lower surface of the skull attachment member and the lower surface of the locking member are generally aligned in a common plane, and an opened state wherein the lower surface of the skull attachment member and the lower surface of the locking member are not aligned in a common plane.

BRIEF DESCRIPTION OF THE DRAWINGS

Various aspects lead fixation devices will now be presented in the detailed description by way of example, and not by way of limitation, with reference to the accompanying drawings, wherein.

DETAILED DESCRIPTION

Disclosed herein are embodiments of a hinged lead fixation device intended to be implanted on the surface of skull to secure a brain lead or any other similarly elongated catheter or medical device (hereafter leads) relative to the skull surface with minimal stress to the lead. The lead fixation device allows the body of a lead to be secured at or along a surface of a skull at a location between the point where the lead exits the skull and the point where the lead connects to an implanted medical device.

The embodiments are described primarily with reference to the lead being an electrode-bearing lead, as might be used in an application for deep brain stimulation or direct brain stimulation such as the responsive stimulations applications by NeuroPace, Inc. of Mountain View, Calif. It should be appreciated, however, that the lead fixation devices may be used with good results to secure a segment of a different type of medical device, such as a catheter or other medical instrument (with a diameter compatible with the accessory), relative to a surface of the skull prior to and/or during use of the medical device in its intended application.

Overview of Procedures to Implant Brain Leads

For purposes of illustration, procedures to implant a depth lead and a cortical strip lead will be described with reference to a responsive neurostimulation system, in which a surgeon commonly uses both lead types.

Figure 1A:
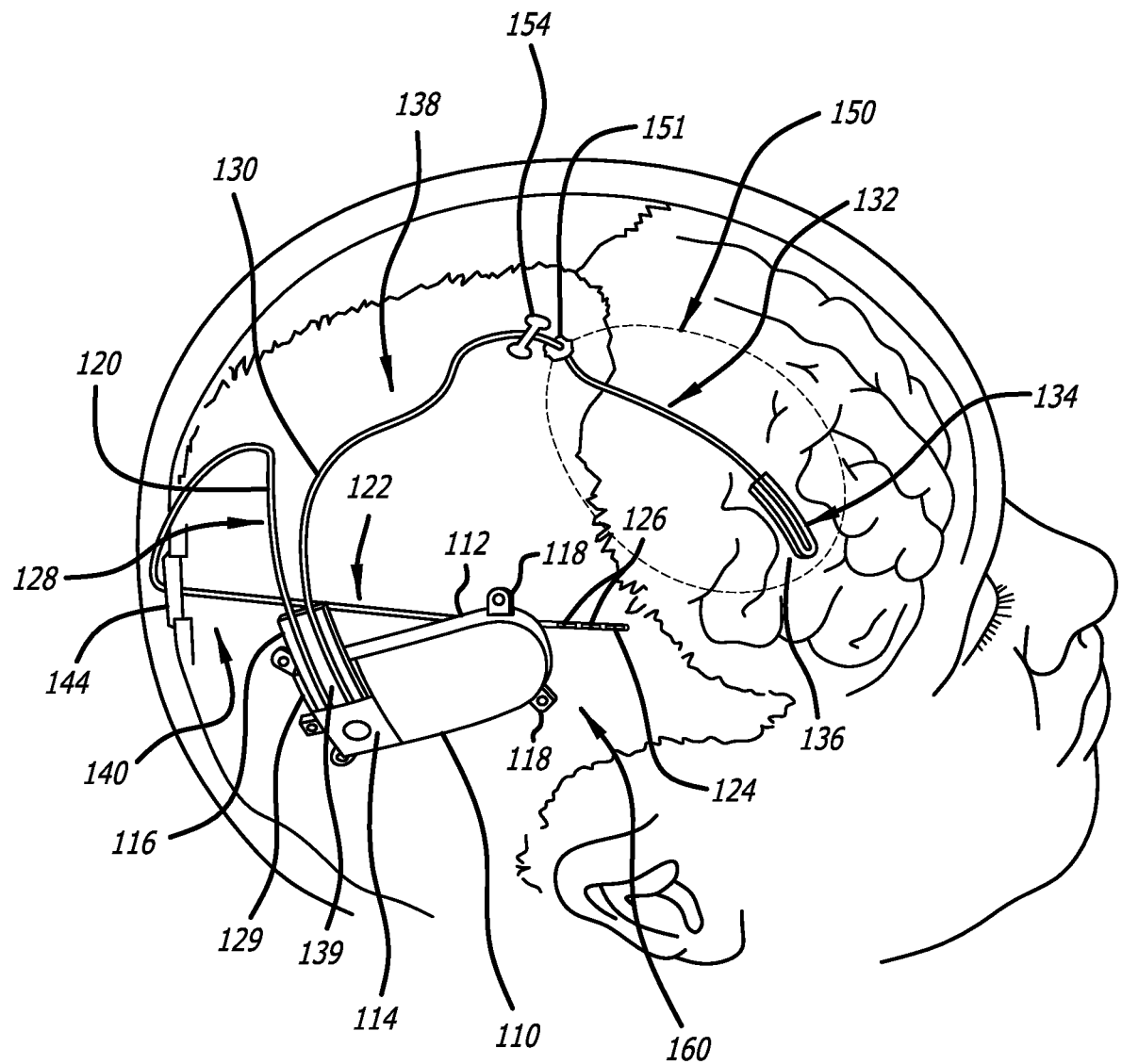
FIG. 1A is a schematic of a patient's cranium showing implanted components of a neurostimulation system, including leads and a neurostimulator, and related surgical accessories, including a burr hole cover and a lead fixation plate.

With reference to FIG. 1A, a neurostimulator 110 and leads 120, 130 of a responsive neurostimulation system are shown schematically, implanted in a patient. To implant a lead, the surgeon needs access to the brain. A surgeon may gain access to the brain for purposes of implanting a lead by creating an opening through the skull. A opening may be created by drilling a hole through the skull, by performing a craniotomy (temporarily removing a bone flap from the skull and replacing the flap after access to the brain is no longer needed) or by performing a craniectomy (permanently removing a bone flap from the skull). Such opening may be used exclusively for lead implant purposes, or may be used for another/additional purpose (for example, the surgeon can first deliver a lead to a target through an opening formed as part of a craniectomy, then use the same opening to implant another medical device, such as a neurostimulator). The term "skull hole" is used herein to refer to any category of opening formed in a patient's skull to gain access to the subdural spaces and to the brain.

In FIG. 1A, three skull holes have been formed: a burr hole 140 for purposes of implanting a depth lead 120, a craniotomy 150 for purposes of implanting a cortical strip lead 130, and a craniectomy 160 in which a ferrule or tray 112 and a neurostimulator 110 are ultimately implanted. More particularly, the surgeon may use an air-powered drill to form an annular burr hole 140 of a diameter between 5-30 mm, with 14 mm being a commonly-used diameter, for purposes of implanting a depth lead 120. In some cases a surgeon may choose to use a smaller diameter hole through which to implant a lead. For example, a surgeon may choose to use a hand-held twist drill to create a hole with a diameter on the order of less than 5 mm (depending on the diameter of the twist drill bit: a common one results in a 3.2 mm diameter hole). A skull hole formed using a twist drill is sometimes referred to as a "twist drill hole". Using appropriate tools, the surgeon may also perform a craniotomy 150 for purposes of implanting a cortical strip lead 130, and additionally a craniectomy 160 in which to ultimately situate a neurostimulator at the patient's skull.

In FIG. 1A, a distal portion 122 of the depth lead 120 extends into the patient's brain tissue from a 14-mm burr hole 140, and a proximal portion 128 extends proximally from the burr hole where it is plugged in at a proximal end 129 to a connector 114 of an implanted neurostimulator 110. A distal portion 132 of a cortical strip lead 130 extends from a fissure like hole or opening 151 at an edge of the craniotomy 150 onto a surface of the patient's brain, between the brain and the dura mater (not shown), and a proximal portion 138 extends proximally from the hole where it is plugged in at a proximal end 139 to the connector 114. The neurostimulator 110 has a strain relief 116 in the location where the proximal ends 129, 139 of the leads connect, to discourage the leads from unintentional disconnection.

A distal end 124 of the depth lead 120 includes a plurality of electrodes 126 (three are shown in FIG. 1A), that can be used either for sensing electrographic activity from the brain or for delivering a therapy of electrical stimulation to it in an effort to modulate neural activity (e.g., lessen the severity of a seizure). Conductors extending the length of the lead body (not shown) and connected at the connector 114 to the neurostimulator 110 allow the neurostimulator to process the sensed signals and to generate the stimulation signals. A distal end 134 of the cortical strip lead 130 ends in a paddle 136 that, on a brain-facing surface thereof (not shown in FIG. 1A), exposes another plurality of electrodes (e.g., four) to the brain surface underneath the dura mater. These electrodes are also in electrical communication with the neurostimulator 110 via conductors in the cortical strip lead 130 and the connection at the connector 114.

In addition to the burr hole 140 or the craniotomy 150 opening 151, a lead, especially of the cortical strip lead type, may be implanted using another opening in the cranium. More specifically, to implant the neurostimulator 110, the surgeon cuts a craniectomy 160 hole using a template that approximates the shape of the neurostimulator. The surgeon fits a tray or "ferrule" 112 into the hole and attaches or otherwise secures it to the cranium, for example, using bone screws and/or folding tabs 118 providing on the tray. The surgeon then situates the neurostimulator 110 into the tray 112. However, before placing the tray 112, the surgeon can use the craniectomy 160 hole to implant a cortical strip lead, such as the cortical strip lead 130, and then connect the proximal end thereof to the neurostimulator connector. (FIG. 1A does not show any lead implanted using the craniectomy 160 in which the tray 112 and neurostimulator 110 are situated.)

Figure 1B:
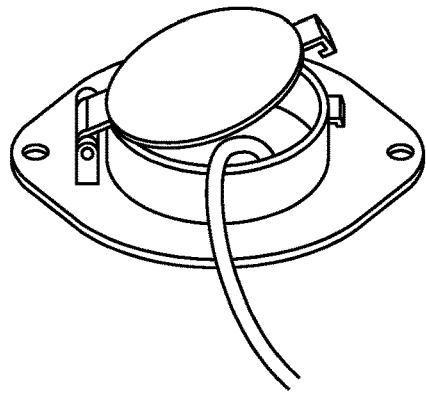
FIGS. 1B and 1C are illustrations of known burr hole covers.
Figure 1C:
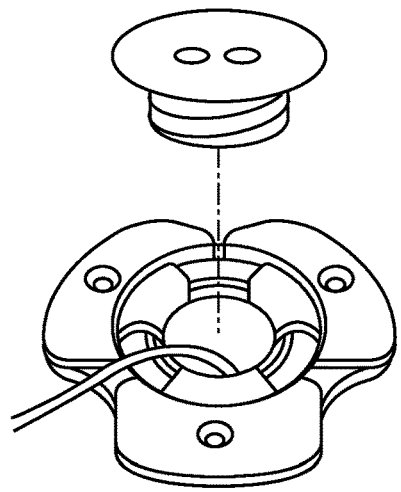

Both of the implanted leads 120, 130 in FIG. 1A are shown secured with known lead fixation accessories. The depth lead 120 implanted through the burr hole 140 is shown secured with a burr hole cover 144 which substantially fills the 14-mm diameter burr hole except for an aperture therethrough that permits passage of the lead body. Examples of lead fixation accessories designed for burr holes are illustrated in FIGS. 1B and 1C.

Some burr hole lead fixation devices are designed for use with mechanical parts that need to be actuated in order to achieve fixation of the lead body, and others rely on friction fit or compression to limit movement of the lead relative to the device. Some require at least one element of the accessory to be put in place before a procedure to implant a lead is begun. Some allow fixation only after any stiffening element used in implanting the lead has been removed. With reference to FIG. 1B, a burr hole lead fixation accessory manufactured by Medtronic, Inc. under the tradename "STIMLOC" uses several interlocking parts to secure a lead body. With reference to FIG. 1C, a two-piece burr hole cover manufactured by NeuroPace, Inc. relies in part on fitting a portion of the lead body into a groove in base element to reduce the likelihood that further manipulation of the lead portion extending proximally of the skull hole (e.g., to connect the lead to an implanted neurostimulator) will translate to movement of the distal end away from the target.

Figure 1D:
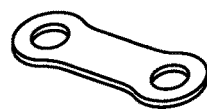
FIG. 1D is an illustration of a known lead fixation plate.

In FIG. 1A, the cortical strip lead 130 implanted through the craniotomy 150, and having a proximal portion 138 extending from the opening 151 at an edge of the craniotomy onto the surface of the skull is secured at a point on the lead body just proximal of where the lead body extends out of the hole, with a cranial plate 154. The cranial plate 154 is situated over the lead body and then secured to the surface of the skull on either side of the lead body with bone screws. Because of its shape, the type of cranial plate 154 shown in FIG. 1A is commonly referred to as a "dog bone". One such plate is shown in FIGS. 1D and 1s manufactured under the tradename "MATRIXNEURO" by Synthes CMF. The cranial plate 154 compresses the lead body to prevent lateral movement of the lead at the point of fixation to the skull. If the compression is inadvertently excessive (e.g., by overtightening of the screws or by a patient pressing down on the plate), the integrity of the lead may be compromised (e.g., the conductors between the electrodes at the lead distal end and the connector at the lead proximal end may be shorted).

The target for a depth lead 120 is usually more precise than the target for a cortical strip lead 130, at least in an application where the condition is epilepsy. That is, the target for a depth lead 120 is usually a particular structure in the brain, such as the subthalamic nucleus (STN) or the cingulate gyrus. The target for a cortical strip lead 130 may be somewhat more forgiving of imprecision, that is, the electrodes on the distal end 124 of the strip lead 130 may be destined to cover the general area on the surface of the brain where epileptic activity is believed to be focused. Thus, it may be especially beneficial to limit movement of the distal end of a depth lead once it has been placed at the target.

In part because of the need for precision and in part because the lead is being implanted into brain tissue as opposed to on a surface of it, a depth lead 120 is most often implanted using some form of stereotaxy (e.g., with a frame affixed to the patient's skull or a "frameless" version of it). Stereotactic procedures are well known and will not be described herein to any great degree. Briefly, however, one common method uses frame-based stereotaxis to approach a target or targets through a skull hole. The patient is given a local anesthetic and a rigid frame or fixation device is attached to the patient's head, and the brain is imaged (e.g., with a CT scan). The location of the target(s) is calculated based on a 'co-registration' of the images and the frame, fiducials or other registered points on the head. Then, the patient is sedated for surgery, the scalp is incised, and one or more skull holes are formed in the patient's cranium, each at a location that will allow an appropriate trajectory to the deep brain target(s).

A hole in the skull is often formed with some standard diameter, owing to the drills typically available in the operating room to create it. When an air drill is used to create a hole in the skull with a diameter of 5 mm or greater, the skull hole is often referred to as a "burr hole." Surgeons create standard-sized burr holes, because there are surgical accessories intended for use with burr holes that are intended for use with certain burr hole diameters, such as 14 mm. However, the diameter of a brain lead may be much smaller than that of a burr hole, because 14 mm is on the order of ten times greater than the diameter of the lead to be implanted. For example, some brain leads manufactured by NeuroPace, Inc. have a diameter of only 1.27 mm. Therefore, in some cases a surgeon may choose to use a smaller diameter hole through which to implant a lead. For example, a surgeon may choose to use a hand-held twist drill to create a twist drill hole with a diameter on the order of less than 5 mm.

Figure 2:
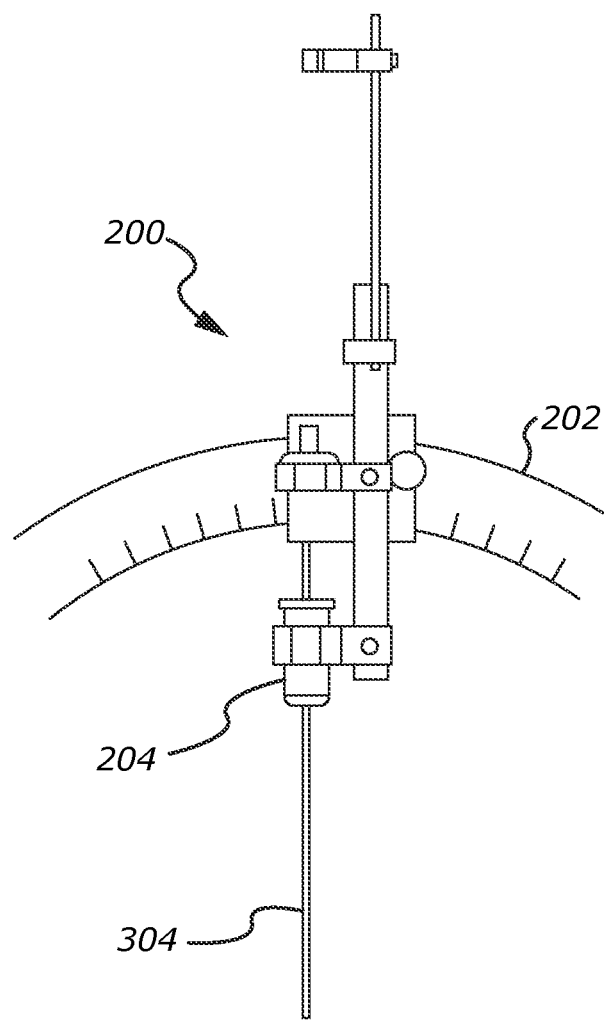
FIG. 2 is an illustration of some components of stereotactic equipment that may be used in a standard stereotactic procedure with a frame to implant a depth lead in a patient's brain.
Figure 3:
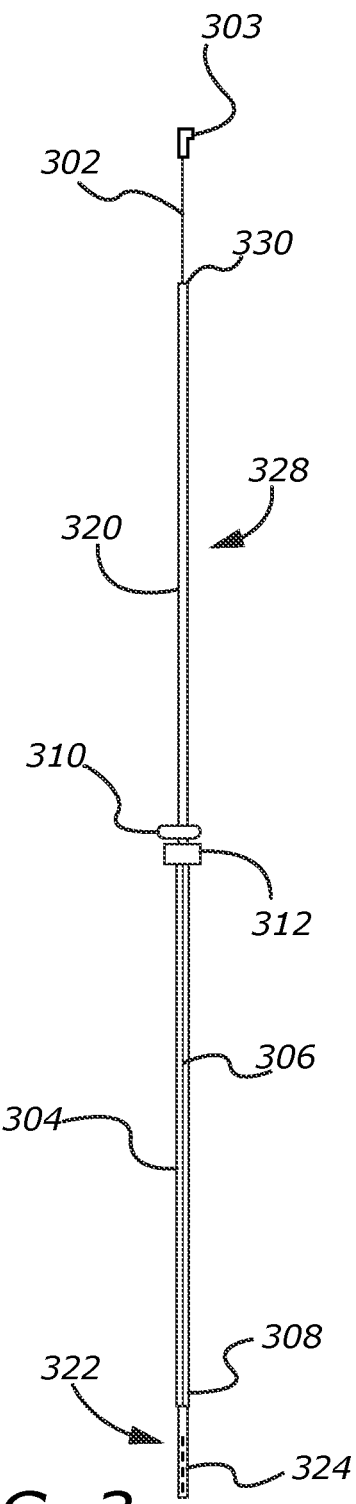
FIG. 3 is an illustration of a cannula (with a depth lead inserted therein) that may be used during a procedure for implanting a depth lead.

Referring now to FIGS. 2 and 3, part of the stereotactic equipment 200 is secured to the patient's skull using a frame, a portion of which is shown as a graduated element 202 in FIG. 2, and a guide tube 204 is oriented to provide the desired trajectory. The guide tube 204 has an inner lumen of sufficient diameter to receive a cannula 304. The cannula 304 is also formed as a cylinder, typically made of a metal, such as stainless steel, and has an inner lumen with a diameter sufficient to slidably receive first an inner rod (not shown) and thereafter a depth lead (the distal end 324 of a depth lead 320 is shown in FIG. 3).

The cannula 304 may be provided with a slot 306 running along its entire length so that the lead body can be extracted from the cannula without having to retract the cannula over the proximal end 330 of the lead. Thus, if the cannula 304 is slotted, the slot 306 must be dimensioned so as to allow the proximal portion of the depth lead 320 that extends proximally of the skull hole to be separated from the cannula through the slot. The depth lead 320 also has an inner lumen running through most of the length of the lead in which a stiffening element, such as a stylet, is removably disposed. (In FIG. 3, a stylet 302 is shown extending proximally of the depth lead 320). The stylet 302 may have a plastic member or stylet handle 303 at its proximal end that the surgeon can grab to extract the stylet more easily from the lead inner lumen.

One or more stop gauges may be configured so that they can encircle the proximal portion of either or both of the cannula 304 or the depth lead 320 to guard against advancing the distal end of the cannula or the depth lead beyond the target (not shown in FIG. 2 or 3). For example, the depth lead 320 may be measured in the operating room to identify a location on a proximal portion that, once the lead is being routed to the target, the surgeon can use to gauge when the lead has been advanced far enough (or to some not-to-exceed distance) into the tissue. This location on the proximal portion can be demarcated by fitting a stop gauge 310 around the lead body.

Manipulating the appropriate controls on the stereotactic equipment, the cannula 304 with the inner rod (not shown) in place is advanced into the brain. The inner rod discourages brain tissue from backing up into the cannula lumen as the cannula creates a path to the target for the lead. When the cannula 304 is advanced as far as intended, the surgeon withdraws the inner rod, and replaces it with the depth lead 320, by inserting the distal end 324 of the depth lead (with the stylet 302 in place) into the proximal end 312 (or top) of the cannula.

FIG. 3 shows a cannula 304 with a depth lead 320 inserted within the cannula inner lumen. A proximal portion 328 of the depth lead 320 extends proximally of a proximal end 312 of the cannula 304, and a distal portion 322 of the depth lead extends distally of a distal end 308 of the cannula 304. The stylet 302 is disposed in an inner lumen of the depth lead 320 and traverses substantially the full length of the depth lead 320, except for the very distal end 324 thereof. The stylet 302 is shown extending proximally of the proximal end 330 of the depth lead 320, with a stylet handle 303 at the proximal tip. The stylet 302 lends sufficient stiffness to the lead 320 while it is being manipulated during the implant procedure (e.g., to insert it into the cannula lumen. The stylet handle 303 makes it easier to remove the stylet 302 from the lead 320 before the procedure is over. It will be appreciated that in a typical stereotactic procedure, even when the depth lead 320 is inserted into the cannula 304 and after the lead distal end 324 has been delivered to the target, there is enough excess lead length so that a portion of the lead body will extend proximally of the proximal end 312 of the cannula, so that the lead at a point on the proximal portion 328 thereof can be grasped above the proximal end 312 of the cannula 304.

After the step in the procedure where the surgeon has the distal end 324 of the lead 320 where he or she wants it, the cannula 304 is removed while the lead is separated from the cannula through the slot 306. After the cannula 304 is removed, it is undesirable for subsequent steps to move the distal end 324 of the lead away from the target. But preventing that from happening can be challenging because, after the cannula 304 is removed, the stylet 302 in the inner lumen of the lead 320 still has to be extracted from the lead body before the procedure is complete. The force applied in pulling out the stylet 302 may tend to retract the distal end 324 of the lead along with it, so removing the stylet is another step which may result in dislodging the lead away from the target. A lead fixation device that addresses the foregoing issue is disclosed in U.S. Patent Application Publication No. 2020/0171299, the entire disclosure of which is incorporated herein by reference.

Furthermore, some form of lead fixation device typically is used to secure a proximal portion of the implanted lead at or near the skull hole or otherwise somewhere on the surface of the skull, to discourage relative movement between the implanted distal portion of the lead and the proximal portion of the lead after the procedure is complete. The step is another opportunity for unwanted displacement of the distal end of the lead from the target. The hinged lead fixation device disclosed below addresses the foregoing issue.

Hinged Lead Fixation Devices

With reference to FIGS. 4A-8B, described are embodiments of a hinged lead fixation device 400, 700 configured to compress against a lead body to thereby secure the lead body relative to a skull surface adjacent a skull hole. The lead fixation device 400, 700 prevents or at least significantly reduces movement of the lead body either further into a skull hole or out of a skull hole after implant of the lead. The hinged lead fixation device 400, 700 secures a portion of the lead relative to a skull surface such that the portion rests on and along a skull surface, in a generally parallel arrangement with the skull surface.

The lead fixation device 400, 700 includes a skull attachment member 402, 702 configured to be secured to the skull and a locking member 404, 704 that is associated with the skull attachment member through a hinge mechanism 406, 706. The lead fixation device 400, 700 includes a passageway 408, 708 that is configured to receive a portion of a lead body.

In one configuration, the passageway 408, 708 is defined by an arcuate recess formed in the locking member 404, 704. The arcuate recess may be, for example, a semi-circular recess. In another configuration, the lead fixation device 400, 700 includes a flexible compression mechanism 410, 710 that defines the passageway 408, 708. The flexible compression mechanism 410, 710 is associated with the locking member 404, 704 and may be in the form of a slotted pipe that defines a slot, gap or opening 412, 712 sized to receive a portion of a lead body. The flexible compression mechanism 410, 710 may be, for example, a half pipe or less than a half pipe. In one configuration, the flexible compression mechanism 410, 710 is less than a half pipe, as shown for example in FIG. 4C, in order to provide clearance between the compression mechanism and the side surface of the skull attachment member 402, 702 as the locking member 404, 704 rotates relative to the locking member. The flexible compression mechanism 410, 710 may be positioned in a recess formed in the locking member.

The skull attachment member 402, 702 and the locking member 404, 704 may be formed of a rigid plastic, e.g., PEEK. The compression mechanism 410, 710 may be formed of a material, e.g., silicone, that is softer and more flexible than the material of the skull attachment member 402, 702 and the locking member 404, 704. The compression mechanism 410, 710 may be configured to create a holding effect between the surface of the mechanism and a surface of a lead body that prevents or significantly reduce movement of the lead relative to the lead fixation device 400, 700. For example, the surface of the compression mechanism 410, 710 against which a lead body rests may be textured to create friction between the mechanism and the lead body, or the mechanism may be made of or coated with a material that is somewhat adhesive, e.g., tacky, such that the lead body sticks to the mechanism.

During production of the lead fixation device 400, 700 the locking member 404, 704 may be formed first, with the compression mechanism 410, 710 subsequently being formed over and within a corresponding recess of the locking member to produce an integral, single piece component. For example, the recess of the locking member 404, 704 may be a semi-circular recess formed in a surface of the locking member. Alternatively, the compression mechanism 410, 710 may be formed separate from the locking member 404, 704 and then fixedly secured within a recess of the locking member to produce an integral, single piece component. Integral in either context means the single piece component cannot be disassembled without damaging the structural integrity of one or more of the locking member and the compression mechanism component parts.

The compression mechanism 410, 710 may include portions 414, 714 that extend from either side beyond the perimeter edge 416, 716 of the locking member 404, 704. In one configuration, the portions 414, 714 extend to the perimeter edge 424 of the securing member 402.

In the embodiments in FIGS. 4A-8B, the compression mechanism 410, 710 defines the passageway 408, 708 through the lead fixation device 400, 700. The compression mechanism 410, 710 has a slot, gap or opening 412, 712 that extends along the length of the mechanism, and is characterized by an inner dimension 420, 720 that is configured to receive a portion of a lead body. The inner dimension 420, 720 may be referred to as a diameter or a slot width.

The skull attachment member 402, 702 includes a screw hole 422, 722 configured to receive a bone screw. In one configuration, the skull attachment member 402, 702 has a maximum thickness of 2 mm in the region of the screw hole 422, 722 and tapers downward to a reduced thickness at the perimeter edge 424, 724. The locking member 404, 704 also includes a screw hole 426, 726 configured to receive a bone screw. In one configuration, the locking member 404, 704 has a maximum thickness of 2 mm in the region of the screw hole 426, 726 and tapers downward to a reduced thickness at the perimeter edge 416, 716.

Regarding the hinge mechanism 406, 706, the skull attachment member 402, 702 includes a hinge cutout 442, 742 and a pair of ports 444, 744 extending through the skull attachment member that are configured to receive a hinge pin 448, 748. The hinge cutout 442, 742 is sized to receive a corresponding hinge structure 446, 746 that extends from the locking member 404, 704. During assembly of the lead fixation device 400, 400, the hinge structure 446, 746 is placed in the hinge cutout 442, 742 and a hinge pin 448, 748 is inserted through the ports 444, 744 to thereby mechanically couple the skull attachment member 402, 702 and the locking member 404, 704 together in a manner that enables rotational movement of the components relative to each other about the hinge pin 448, 748.

Figure 4A:
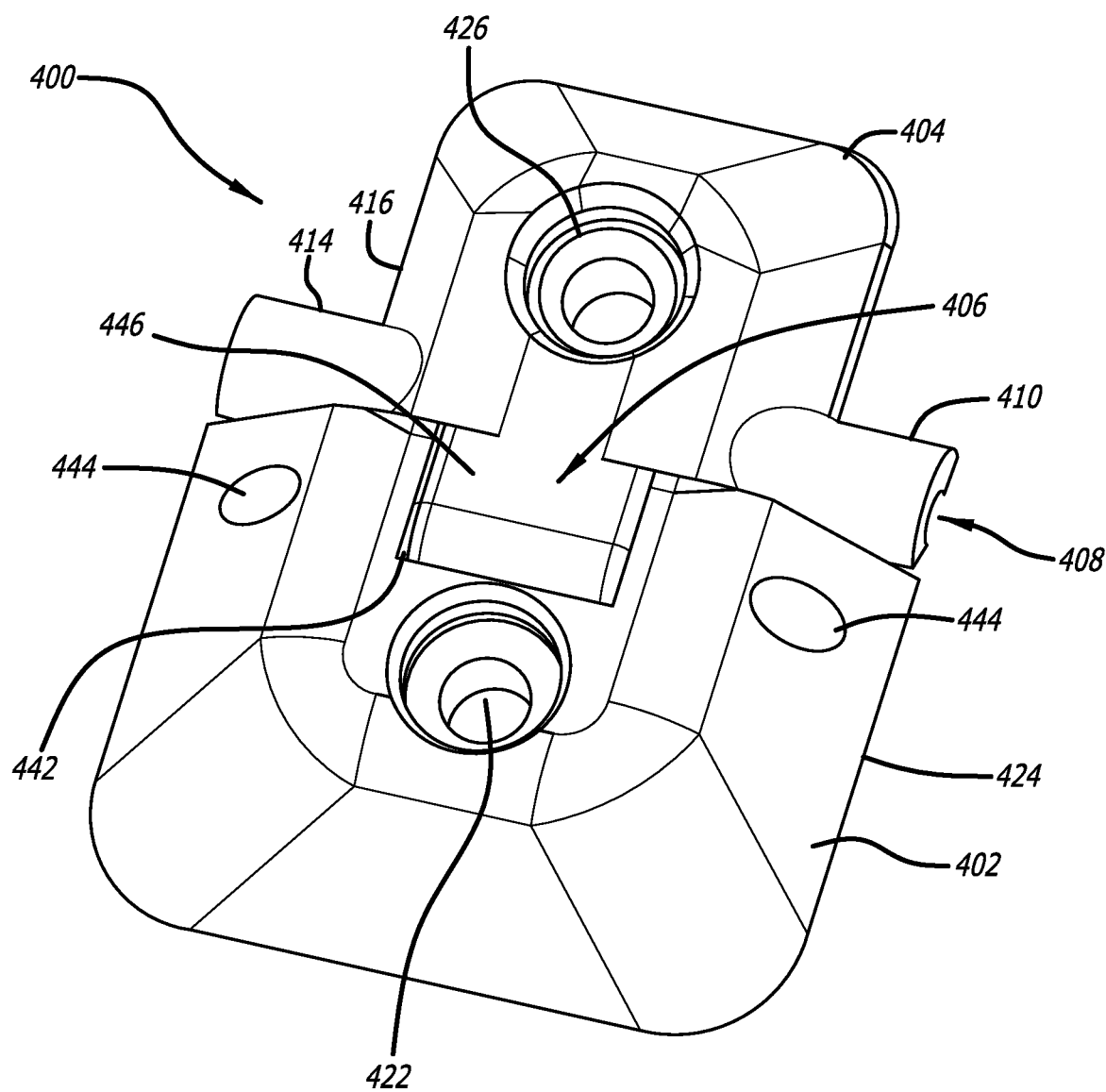
FIGS. 4A-4D are illustrations of a first configuration of a hinged lead fixation device in a closed state.
Figure 4B:
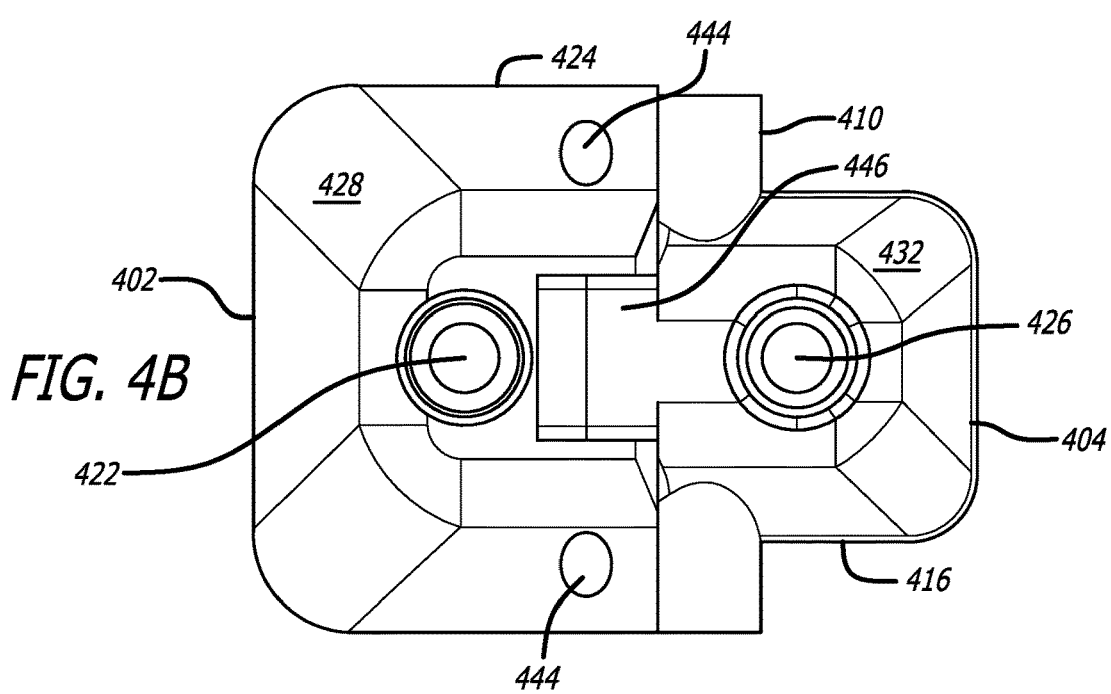
Figure 4C:
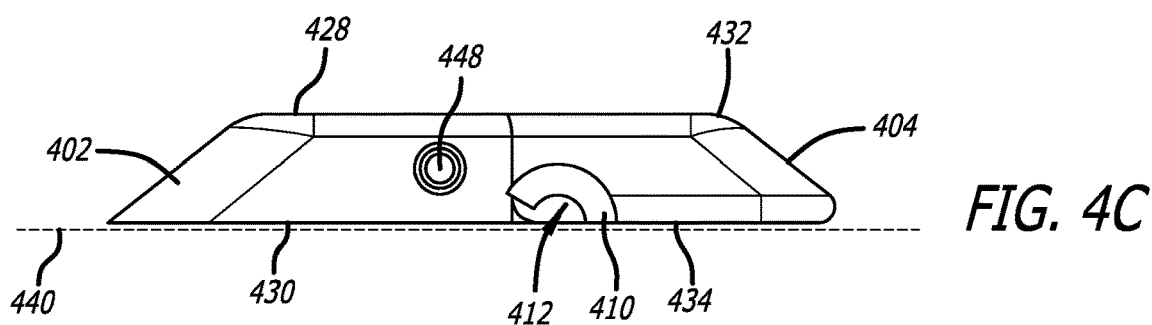
Figure 4D:
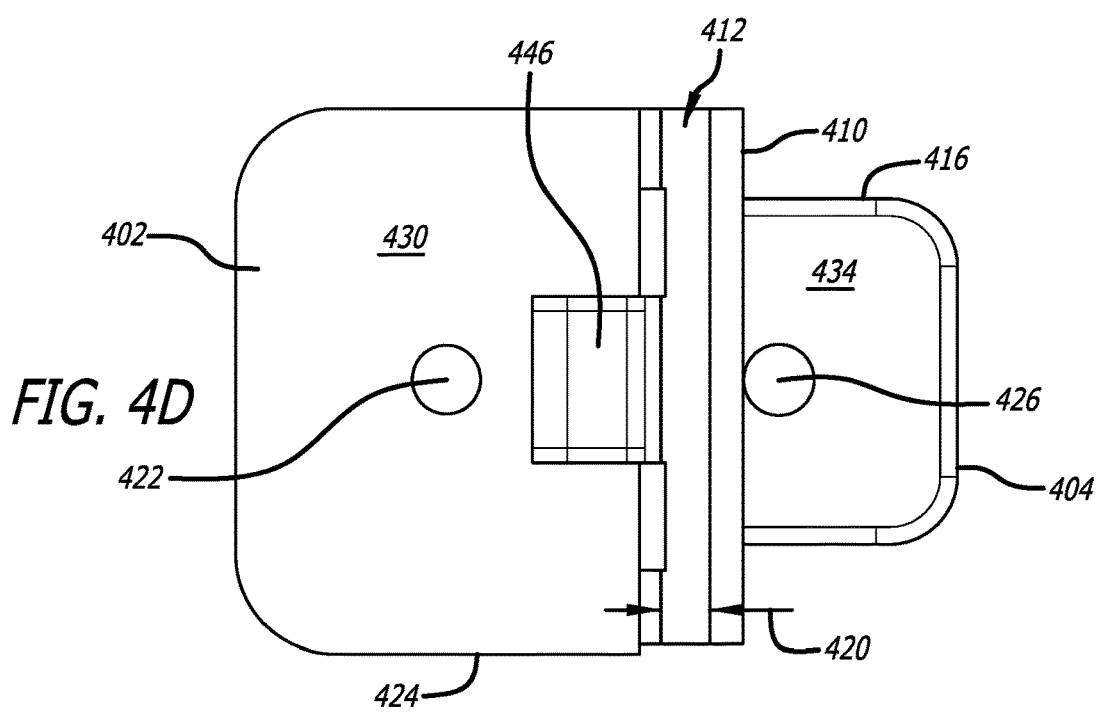
Figure 5A:
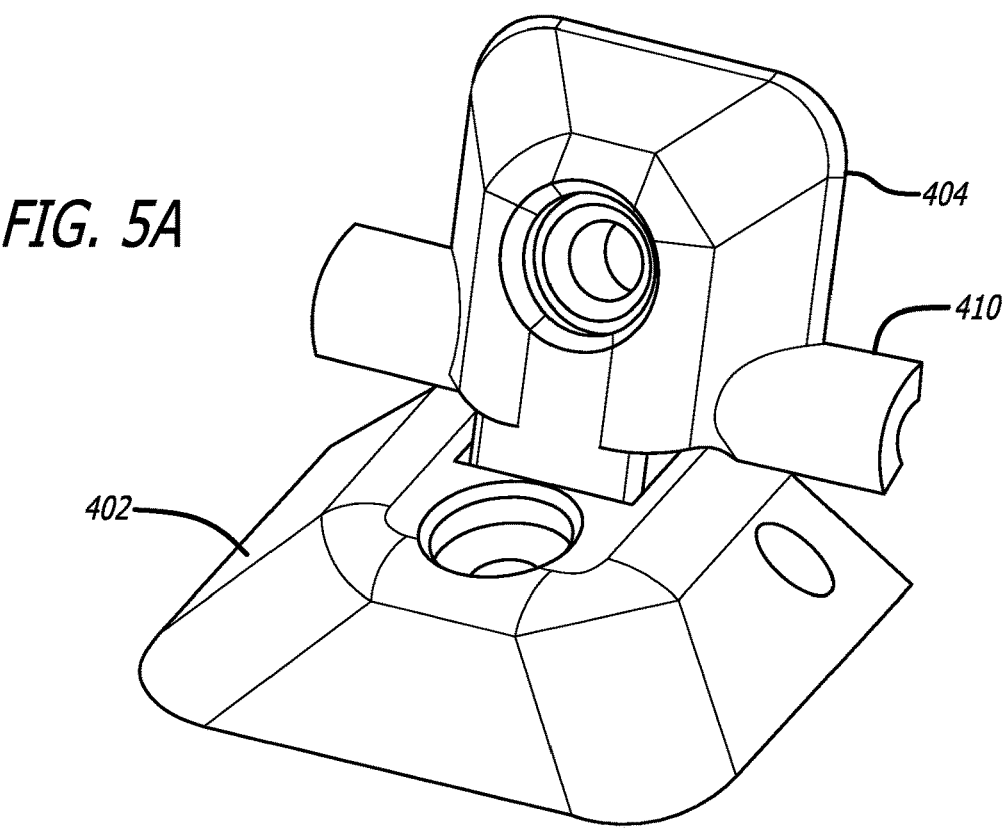
FIGS. 5A and 5B are illustrations of the first configuration of a hinged lead fixation device in an opened state.
Figure 5B:
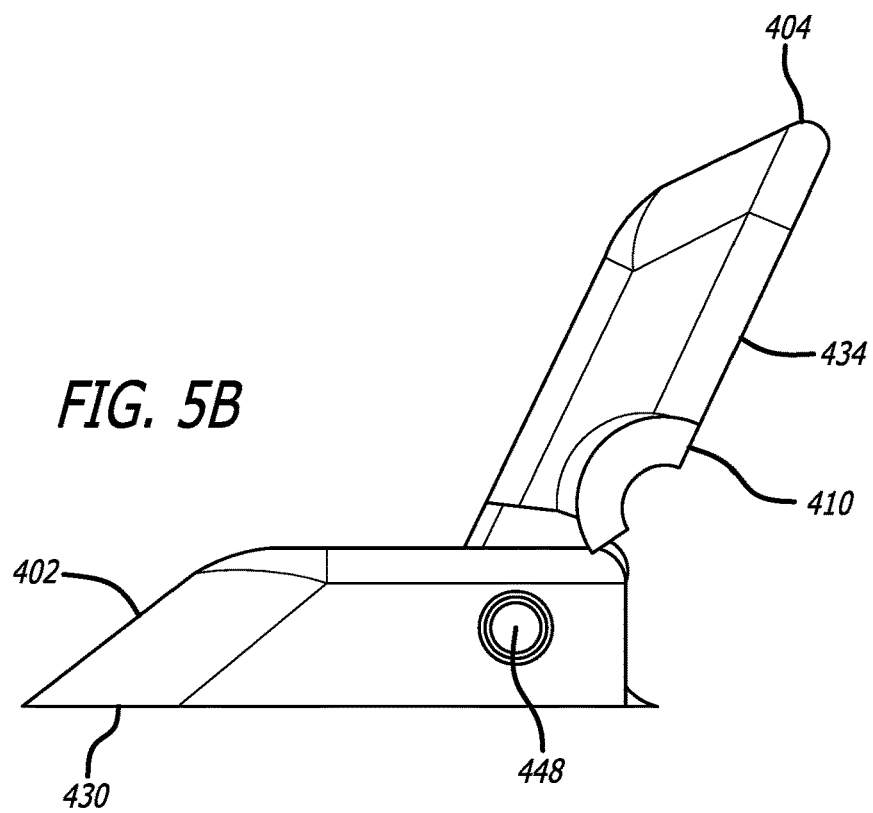
Figure 6A:
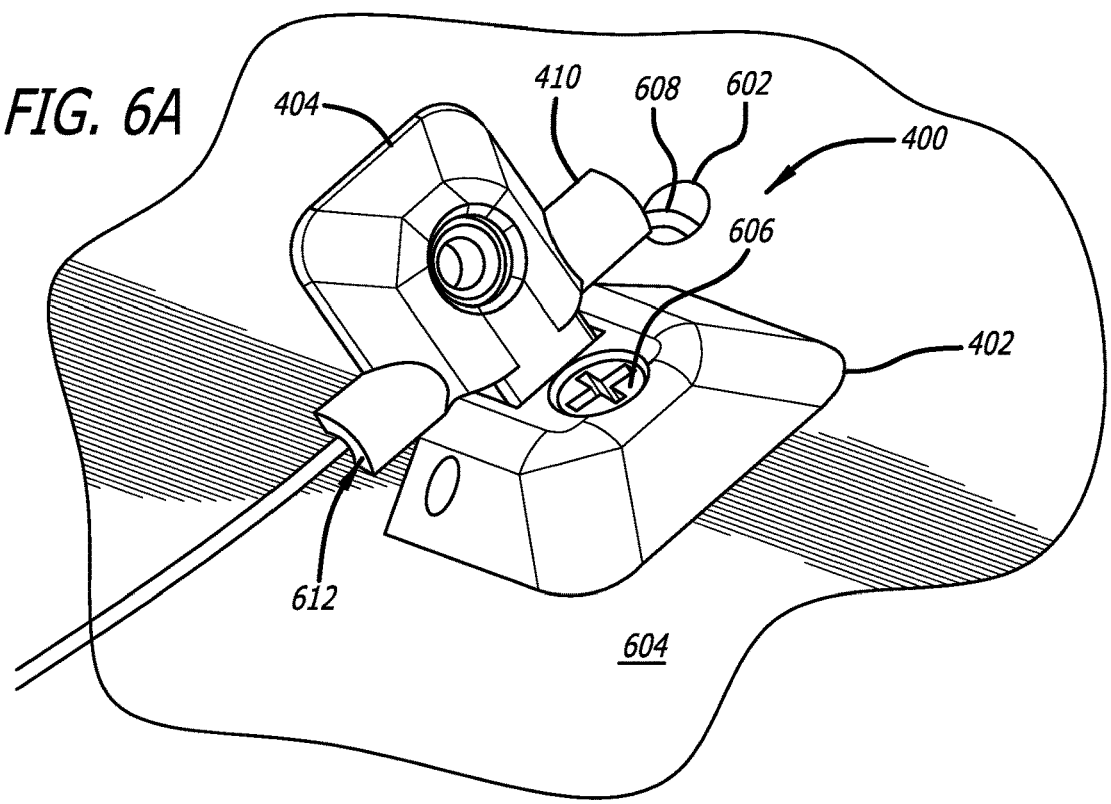
FIGS. 6A and 6B are illustrations of a lead implant procedure using the lead fixation device of FIGS. 4A-4D.
Figure 6B:
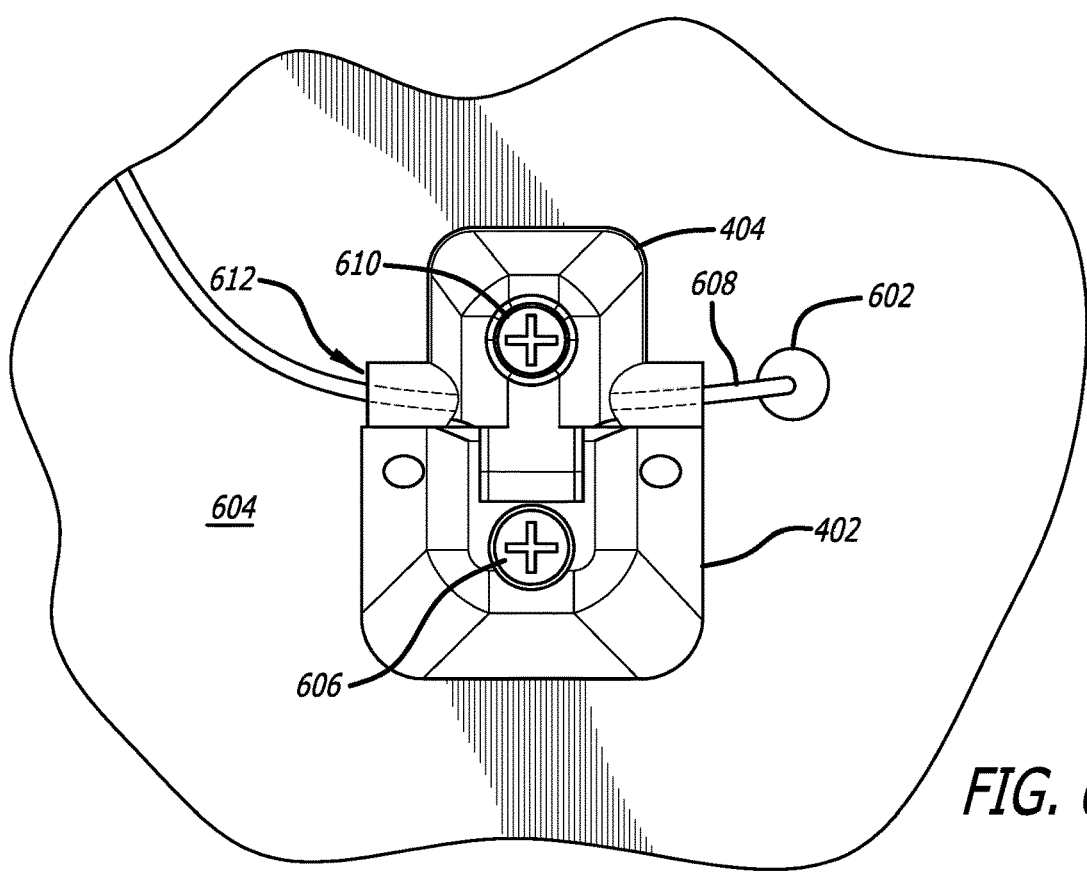
Figure 7A:
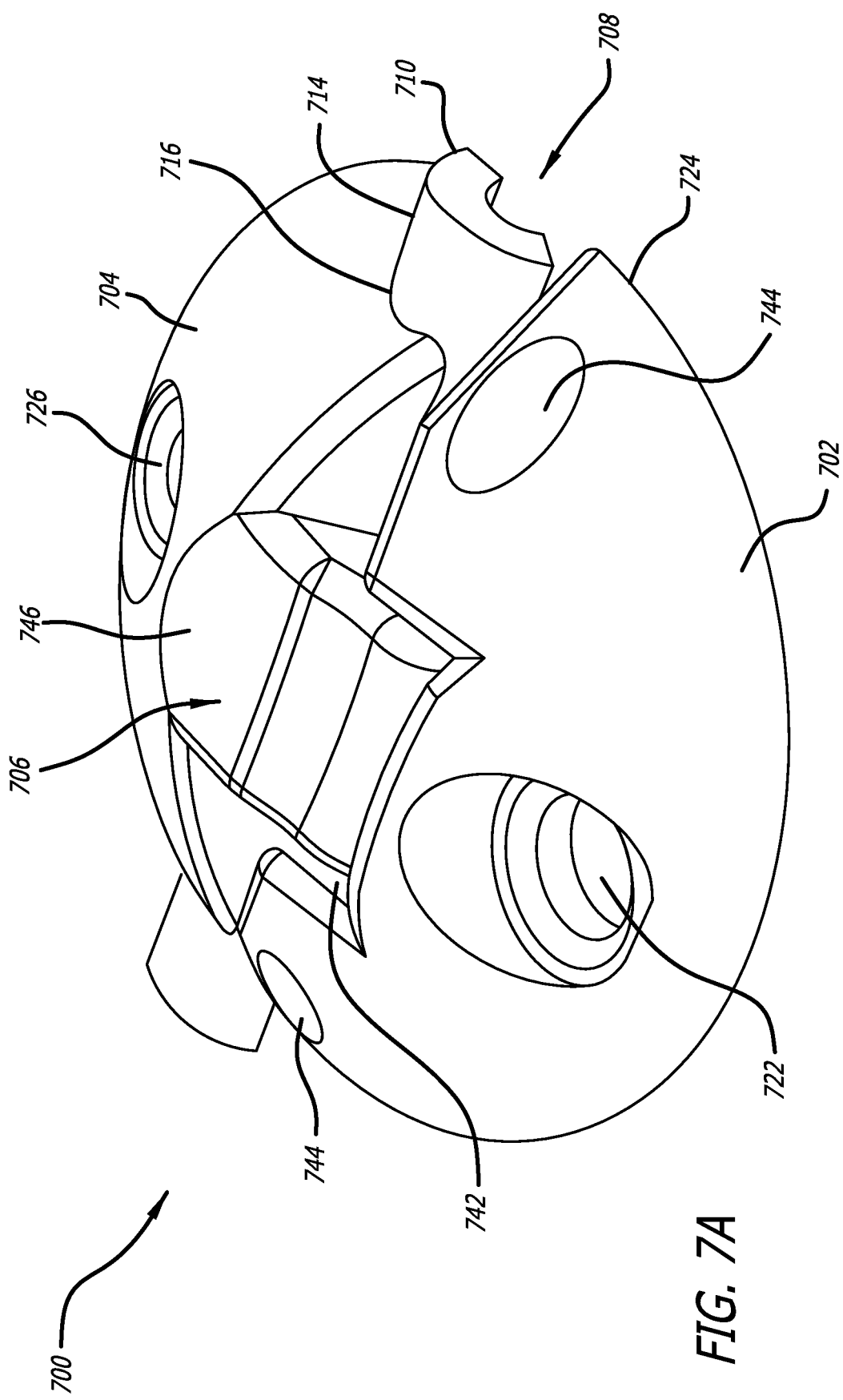
FIGS. 7A-7D are illustrations of a second configuration of a hinged lead fixation device in a closed state.
Figure 7B:
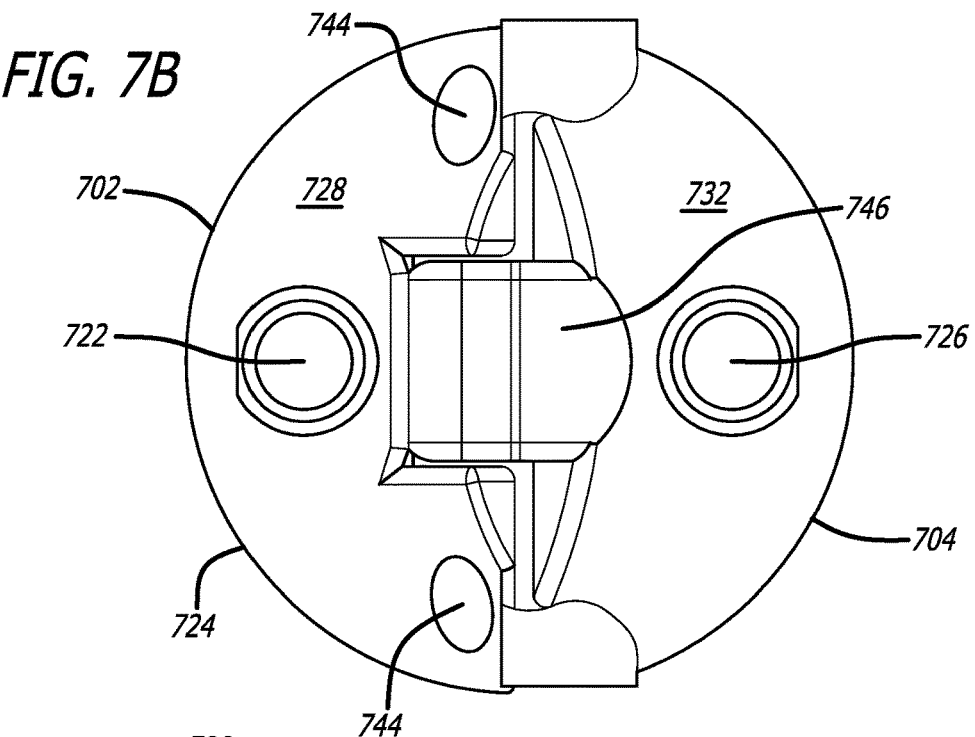
Figure 7C:
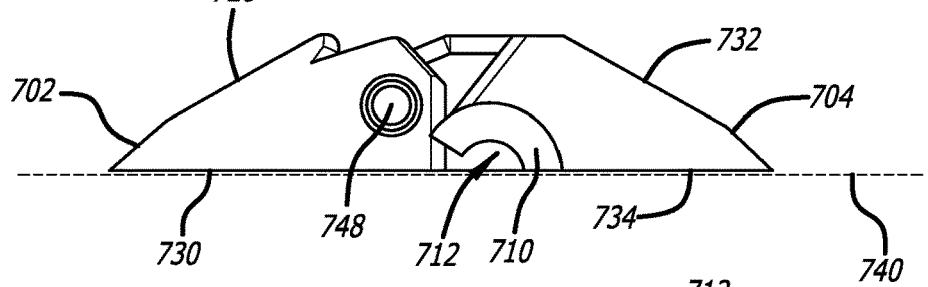
Figure 7D:
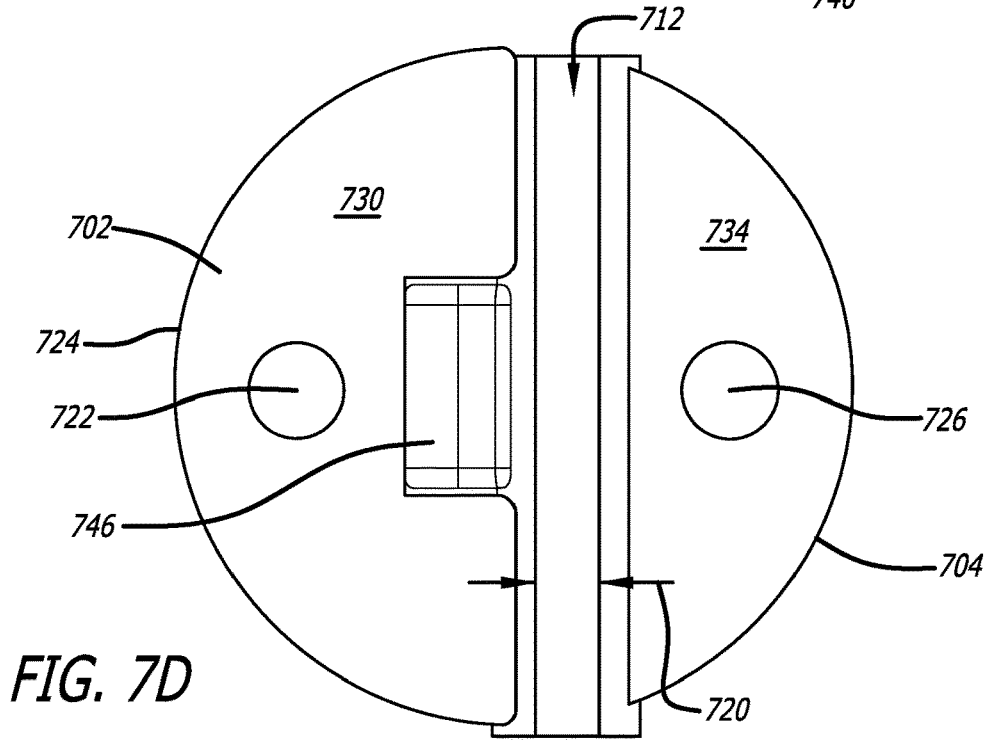
Figure 8A:
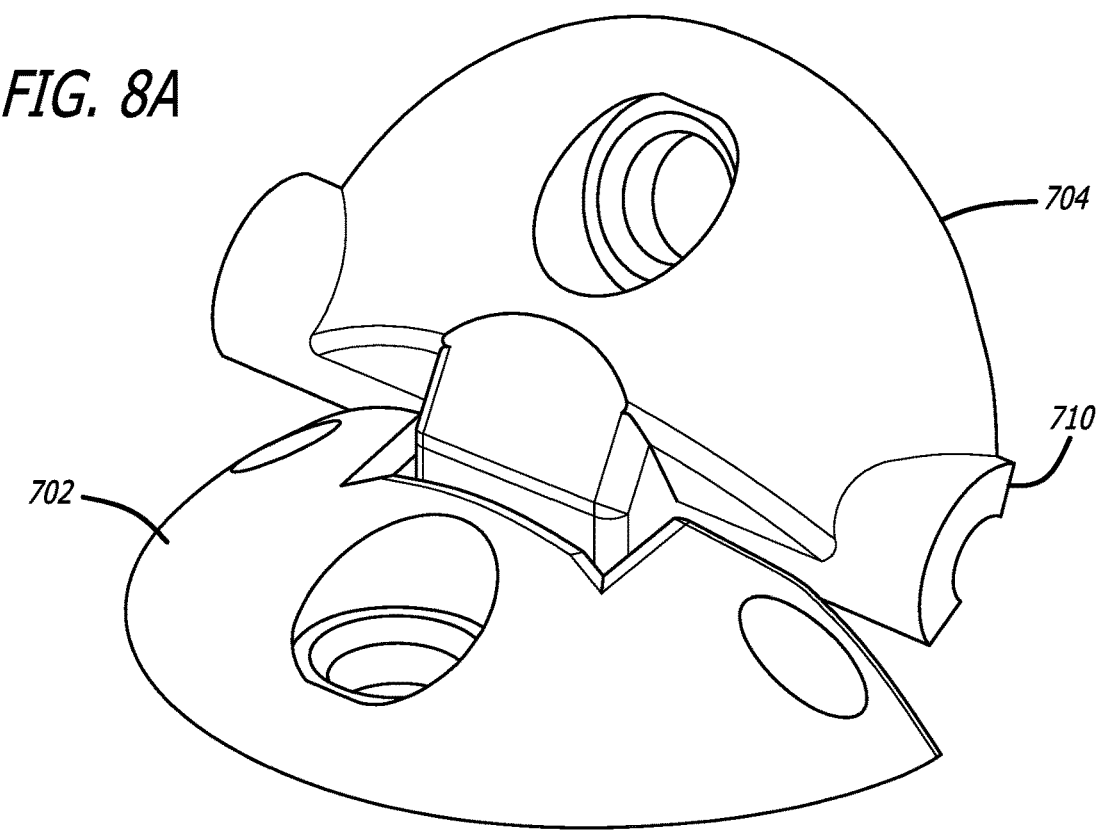
FIGS. 8A and 8B are illustrations of the second configuration of a hinged lead fixation device in an opened state.
Figure 8B:
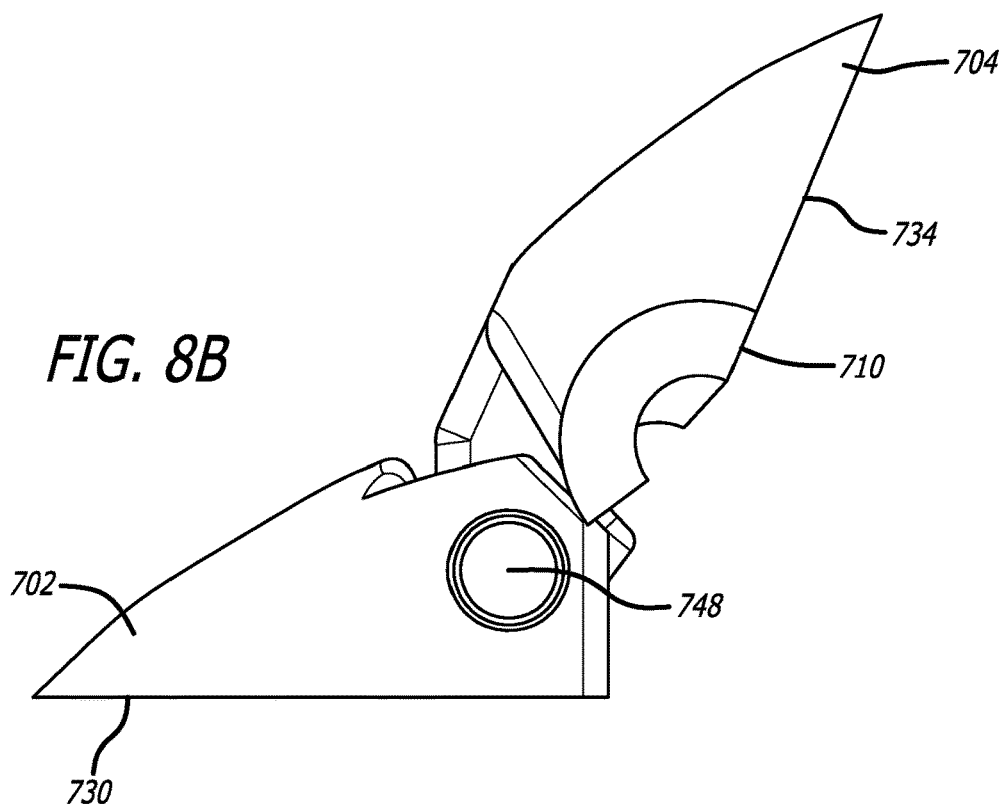

With reference to FIGS. 6A and 6B, an example lead implant procedure using the lead fixation device of FIGS. 4A-5B is provided. A twist drill hole 602 is formed in a location of the cranium using known stereotactic techniques.

With the lead fixation device 400 in a closed state (as shown in FIG. 4A), an end of the compression mechanism 410 is aligned adjacent the twist drill hole 602 and the skull attachment member 402 of the lead fixation device is secured to the surface 604 of the cranium using a bone screw 606.

The lead fixation device 400 is then transitioned or moved to the opened state (as shown in FIGS. 5A, 5B, and 6A) by rotating the locking member 404 about the hinge pin 448, 748 relative to the skull attachment member 402.

A lead 608 is implanted through the twist drill hole 602 using known techniques and a portion of the lead is placed to extend parallel to and on the surface 604 of the cranium and along the side of the skull attachment member 402 as shown in FIG. 6A.

The lead fixation device 400 is then moved to the closed state (as shown in FIGS. 4A and 6B) by rotating the locking member 404 relative to the skull attachment member 402, and while adjusting the position of the body of the lead 608, if needed, so that a portion 612 of the lead body aligns with and is placed in the passageway 408 of the compression mechanism 410 as the locking member is rotated and the lead fixation device is transitioned to the closed state.

The locking member 404 is then secured to the surface 604 of the cranium using a bone screw 610. The force of the compression mechanism 410 against the lead that results from the securing of the locking member 404 to the surface 604 secures the lead in place relative to the surface without pinching or causing damage to the lead. Furthermore, as previously described, the compression mechanism 410, 710 may be configured to create a holding effect, e.g., friction, stickiness, between the surface of the mechanism and a surface of a lead body that secures the lead in place.

Thus disclosed is a lead fixation device 400,700 for securing a portion 612 of a lead 608 relative to a surface 604 of a skull. The lead fixation device 400, 700 includes a skull attachment member 402, 702 having an upper surface 428, 728 and a lower surface 430, 730; and a locking member 404, 704 coupled with the skull attachment member. The locking member 404, 704 also has an upper surface 432, 732 and a lower surface 434, 734. A passageway 408, 708 is associated with the locking member 404, 704 and is configured to receive the portion 612 of the lead 608.

The skull attachment member 402, 702 and the locking member 404, 704 are configured to rotate relative to each other to thereby transition the lead fixation device 400, 700 between a closed state and an opened state. While in a closed state, such as shown in FIG. 4C, the lower surface 430, 730 of the skull attachment member 402, 702 and the lower surface 434, 734 of the locking member 404, 704 are generally aligned in a common plane 440, 740. While in an opened state, such as shown in FIG. 5B, the lower surface 430, 730 of the skull attachment member 402, 702 and the lower surface 434, 734 of the locking member 404, 704 are not aligned in a common plane 440, 740.

In one configuration, the passageway 408 corresponds to a channel formed in the lower surface 434, 734 of the locking member 404, 704. In another configuration, the passageway 408, 708 is defined by a compression mechanism 410, 710 that is associated with the locking member 404, 704. The compression mechanism 410, 710 is formed of a flexible material. The locking member 404, 704 is formed of a material more rigid than the compression mechanism 410, 710.

In one configuration, the compression mechanism 410, 710 is formed of a flexible material and includes a slot, gap or opening 412, 712 along the length of the compression member. The opening 412, 712 faces in the direction of the lower surface 434, 734 of the locking member 404, 704 and is characterized by a slot width or diameter 420, 720. The flexibility of the compression mechanism 410, 710 enables the width 420, 720 of the opening 412, 712 to transition from an initial size to an expanded size that is greater than the initial size. In one configuration, the initial size of the opening 412, 712 is less than the diameter of the portion 612 of the lead that is to be received by the compression mechanism 410, 710 and the expanded size is greater than the diameter the portion 612. The expanded size of the opening 412, 712 is obtained by pushing or forcing the portion 612 of the lead through the opening into the compression mechanism 410, 710. Once the portion 612 of the lead body is seated within the compression mechanism 410, 710 the width 420, 720 of the opening 412, 712 may return to the initial size.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A lead fixation device for securing a portion of a lead relative to a surface of a skull, the lead fixation device comprising:
    a skull attachment member having an upper surface and a lower surface;
    a locking member having an upper surface and a lower surface and associated with the skull attachment member;
    a hinge for coupling the skull attachment member to the locking member; and
    a passageway defined by a compression mechanism and associated with the locking member and configured to receive the portion of the lead,
    wherein the lower surface of the locking member comprises a recess and the compression mechanism is located at least partially within the recess, and
    wherein the skull attachment member and the locking member rotate relative to each other about the hinge while remaining coupled together by the hinge to thereby transition the lead fixation device between:
        a closed state wherein the lower surface of the skull attachment member and the lower surface of the locking member are generally aligned in a common plane, and
        an opened state wherein the lower surface of the skull attachment member and the lower surface of the locking member are not aligned in a common plane.

2. The lead fixation device of claim 1, wherein the passageway corresponds to a channel formed in the locking member.

3. The lead fixation device of claim 1, wherein the compression mechanism comprises an opening along a length of the compression mechanism having a width sized to receive the portion of the lead.

4. The lead fixation device of claim 1, wherein:
    the compression mechanism is formed of a flexible material and comprises an opening along a length of the compression mechanism having a width; and the flexible material of the compression mechanism enables the width of the opening to transition from an initial size to an expanded size that is greater than the initial size.

5. The lead fixation device of claim 4, wherein the portion of the lead has a diameter and the initial size is less than the diameter and the expanded size is greater than the diameter.

6. The lead fixation device of claim 4, wherein the opening faces in the direction of the lower surface of the locking member.

7. The lead fixation device of claim 1, wherein the compression mechanism is formed of a flexible material.

8. The lead fixation device of claim 1, wherein the compression mechanism is configured to create a holding effect between a surface of the compression mechanism and a surface of a lead body.

9. The lead fixation device of claim 8, wherein the surface of the compression mechanism is textured.

10. The lead fixation device of claim 8, wherein the surface of the compression mechanism is coated with an adhesive material.

11. The lead fixation device of claim 1, wherein in an opened state the lower surface of the skull attachment member and the lower surface of the locking member are in different planes at an angle relative to each other.

12. A lead fixation device for securing a portion of a lead relative to a surface of a skull, the lead fixation device comprising:
   a skull attachment member having an upper surface and a lower surface;
   a locking member having an upper surface and a lower surface and associated with the skull attachment member;
   a hinge for coupling the skull attachment member to the locking member; and
   a passageway defined by a compression mechanism and associated with the locking member and configured to receive the portion of the lead,
   wherein the compression mechanism comprises portions that extend from either side beyond an outer perimeter edge of the locking member, and
   wherein the skull attachment member and the locking member rotate relative to each other about the hinge while remaining coupled together by the hinge to thereby transition the lead fixation device between:
      a closed state wherein the lower surface of the skull attachment member and the lower surface of the locking member are generally aligned in a common plane, and
      an opened state wherein the lower surface of the skull attachment member and the lower surface of the locking member are not aligned in a common plane.

13. The lead fixation device of claim 12, wherein the portions extend to an outer perimeter edge of the skull attachment member.

14. A lead fixation device for securing a portion of a lead relative to a surface of a skull, the lead fixation device comprising:
   a skull attachment member having an upper surface and a lower surface;
   a locking member having an upper surface and a lower surface and associated with the skull attachment member;
   a hinge for coupling the skull attachment member to the locking member; and
   a passageway defined by a compression mechanism and associated with the locking member and configured to receive the portion of the lead,
   wherein the locking member is formed of a material more rigid than the compression mechanism, and
   wherein the skull attachment member and the locking member rotate relative to each other about the hinge while remaining coupled together by the hinge to thereby transition the lead fixation device between:
      a closed state wherein the lower surface of the skull attachment member and the lower surface of the locking member are generally aligned in a common plane, and
      an opened state wherein the lower surface of the skull attachment member and the lower surface of the locking member are not aligned in a common plane.

15. The lead fixation device of claim 14, wherein the skull attachment member is formed of a material more rigid than the compression mechanism.

* * * * *